United States Patent [19]
Manz et al.

[11] Patent Number: 5,635,137
[45] Date of Patent: Jun. 3, 1997

[54] REAGENT STORAGE AND REAGENT VESSEL

[75] Inventors: Harald Manz, Kirkkonummi; Juhani Makunen, Veikkola; Jari-Pekka Riekkinen, Espoo, all of Finland

[73] Assignee: Kone Instruments Oy, Espoo, Finland

[21] Appl. No.: 426,249

[22] Filed: Apr. 21, 1995

[30] Foreign Application Priority Data

Apr. 21, 1994 [FI] Finland ................... 941867

[51] Int. Cl.⁶ .................. G01N 35/02; B01L 3/00
[52] U.S. Cl. .................. 422/102; 422/64; 422/104; 206/446; 215/395; 215/396
[58] Field of Search ................ 422/63, 64, 99, 422/102, 104; 436/43, 47, 809, 810; 206/446; 215/395, 396

[56] References Cited

U.S. PATENT DOCUMENTS

| | | | |
|---|---|---|---|
| 4,346,056 | 8/1982 | Sakurada | 422/64 |
| 4,455,280 | 6/1984 | Shinohara et al. | 422/63 |
| 4,764,342 | 8/1988 | Kelln et al. | 422/72 |
| 4,781,891 | 11/1988 | Galle et al. | 422/64 |
| 4,782,945 | 11/1988 | Geiler et al. | 206/203 |
| 4,849,177 | 7/1989 | Jordan | 422/64 |
| 5,322,668 | 6/1994 | Tomasso | 422/104 |
| 5,424,036 | 6/1995 | Ushikubo | 422/64 |
| 5,427,743 | 6/1995 | Markin | 422/104 |

*Primary Examiner*—Long V. Le
*Attorney, Agent, or Firm*—Birch, Stewart, Kolasch & Birch, LLP

[57] ABSTRACT

The invention relates to a frame for the storage of reagent vessels (4) and to a reagent vessel. The frame has a bottom part and a substantially circular rim, and the reagent vessels can be so stored in the frame that they extend to the rim (3) of the frame. The frame is provided with substantially radial partitions (6) for holding the vessels (4) in place. According to the invention, the partitions (6) are provided with auxiliary protrusions (10) placed so that the distance of the auxiliary protrusions from the rim (3) is substantially equal to the distance between two adjacent partitions (6) at the rim and that the distance between two auxiliary protrusions (10) on adjacent partitions (6) is shorter than the distance of the auxiliary protrusions (10) from the rim (3). The side walls of the reagent vessel (4) of the invention are provided with vertical recesses.

17 Claims, 2 Drawing Sheets

REAGENT STORAGE AND REAGENT VESSEL

FIELD OF THE INVENTION

The present invention relates to a frame for the storage of reagent vessels and to a reagent vessel.

BACKGROUND OF THE INVENTION

In previously known analyzers, the reagents needed for analysis are generally stored in bottles or in specially shaped containers or reagent vessels. From these, the reagent is transferred into the analyzing process either by suction through a hose permanently connected to the bottle or by inserting through the bottle mouth a dosing needle into which the reagent is drawn and from which it is passed further into the analyzing process. The bottles or vessels are stored either in a fixed storage space, often provided with a cooling system, or in a movable disc, usually rotatable. In the case of a discoid storage, an optimum space utilization is achieved if the vessel has the shape of a sector. Sector-shaped vessels allow the most efficient utilization of a circular storage area.

Sometimes, however, there is a need to use a different type of vessels, e.g. round bottles, to store reagents. The need for a round bottle may arise e.g. from the fact that it is not economically or otherwise sensible to store a small volume of reagent in a sector-shaped vessel or that a glass bottle is the best or even the only solution to ensure stability of the reagents.

If a sector-shaped vessel and a round bottle are to be firmly positioned in the same frame, this generally requires a separate guide to surround the round bottle with a body of partly or completely sectorial shape. As the space utilization in a round disc has been designed for a sectorial vessel, positioning a round bottle firmly in it without a separate guide is generally not possible.

SUMMARY OF THE INVENTION

The object of the present invention is to achieve a new frame for the storage of reagent vessels, permitting different types of vessel to be stored in the same frame.

The storage frame of the invention allows a sectorial vessel or alternatively a round bottle to be firmly positioned in a storing place in the frame without a separate guide so that the orifice of the container can lie at the same distance from the center of the frame and its bottom at the same level as in the case of a sectorial vessel. In the storage frame of the invention, sectorial reagent vessels and round bottles are held in a circular frame having for each vessel or bottle a storing place retaining the vessel or bottle laterally in position. The retaining elements acting as vessel guides are so designed that they retain a round bottle laterally by two or more sides, but on the other hand they also retain a sectorial vessel whose sides are provided with grooves appropriately placed.

Regardless of whether the container is a round bottle or a sectorial vessel, it can be so placed that its orifice always comes to the same position and its bottom to the same level without separate guides. This allows the application of uniform methods to establish the amount of reagent in a container and to extract a reagent from a container regardless of its shape.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, the invention is described in detail by the aid of an example by referring to the attached drawings which are given by way of illustration only, and thus are not limitative of the present invention, and in which.

DESCRIPTION OF THE PREFERRED EMBODIMENTS

Figure 1:
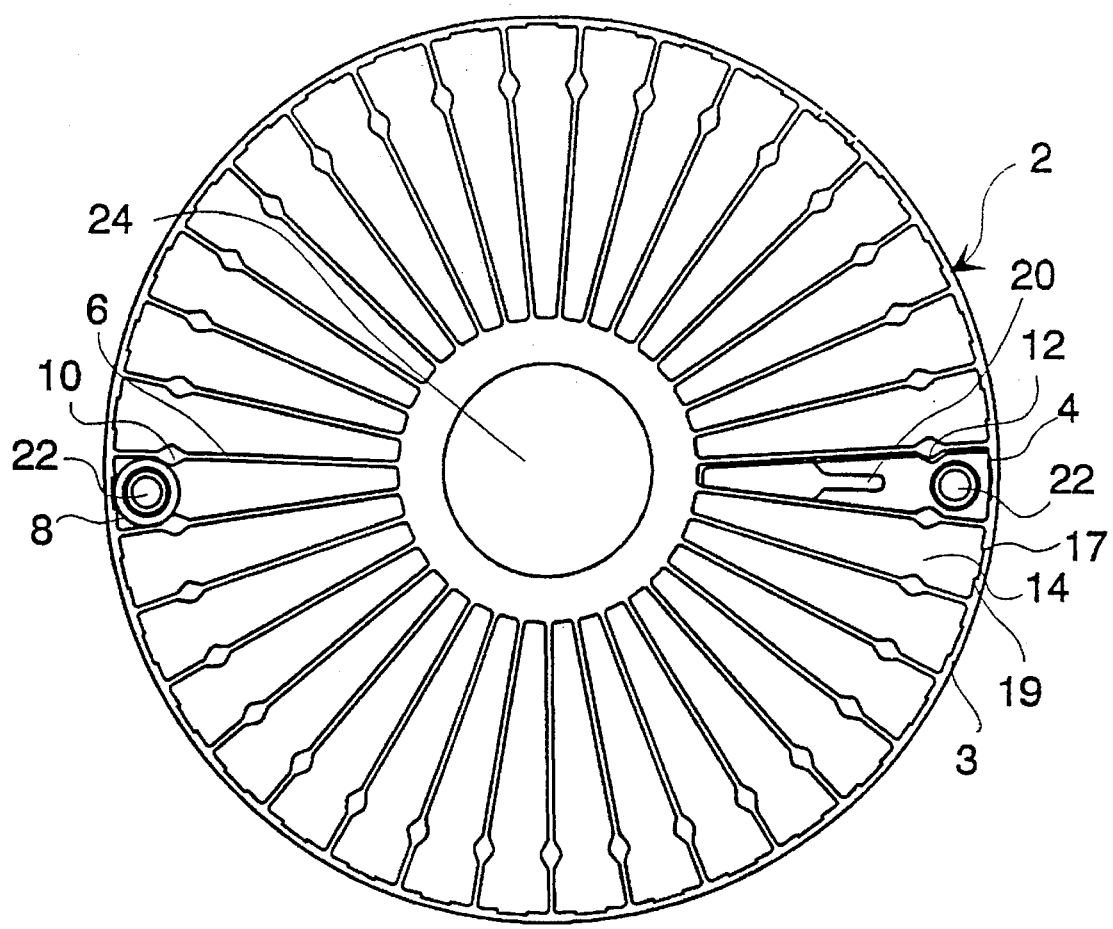
FIG. 1 presents a circular frame and vessels placed in it, in top view.
Figure 2:
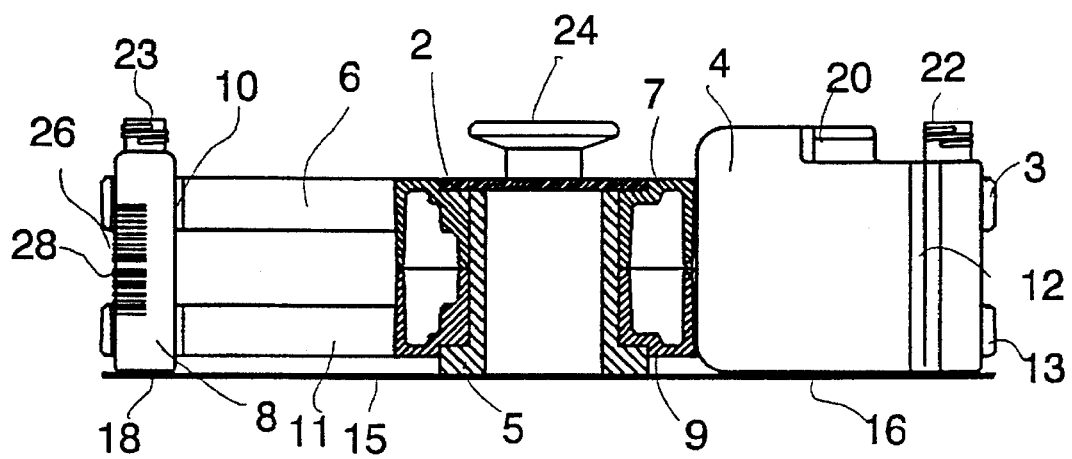
FIG. 2 presents the frame in side view along section A—A in FIG. 1.

FIG. 1 shows a reagent store of an analyzer, consisting of a rotatable circular frame 2, with a reagent vessel 4 and a round reagent bottle 8 placed in it. FIG. 2 depicts the frame in a sectional side view along line A—A. At the center of the frame there is a handle 24 by which the frame can be lifted and moved together with the containers to a place of use or to a storage facility, such as a refrigerator. The central part of the frame consists of a sleeve 5 into which the shaft (not shown) of an actuator designed to rotate the frame is inserted. Placed around the sleeve 5 is an upper support ring 7 and a lower support ring 9. Attached to the upper 7 and lower 9 support rings are radial partitions 6 and 11, respectively. The other ends of partitions 6 are connected to a ring 3 constituting the rim of the frame. Partitions 11 are likewise attached to a ring 13. The underside of the frame is provided with a bottom 5 supporting the vessels 4 and bottles 8 placed in the frame. Although the components of the frame are described above as separate parts, they can be manufactured as a single plastic body e.g. by casting or pressing.

When the vessels 4 are being placed in the frame 2, the radial partitions 6 and 11 of the frame act as guides for the sectorial reagent vessels 4 to be placed between them. Partitions 6 are provided with auxiliary protrusions 10 located at a distance from the rim 3 of the frame to retain the reagent vessels 4 placed in the frame. The auxiliary protrusion 10 is formed by making a protrusion in partition 6. Partitions 11 can be provided with corresponding auxiliary protrusions. The side walls of the reagent vessels are provided with recesses 12 corresponding to the auxiliary protrusions 10, so that the auxiliary protrusions 10 also guide the reagent vessel to its proper position. Formed on the inside of the rings 3 constituting the rim of the frame are stop faces 17 and 19 slightly protruding inwards from the inner surface of the ring. The stop faces and the auxiliary protrusions are so laid out that they will retain a reagent bottle 8 placed in the frame. Thus, the circle corresponding to the outer surface of the bottle 8 is tangent with the stop faces, auxiliary protrusions and the interior ring surface between the stop faces 17 and 19, providing five retaining points for the bottle. The bottle is adequately retained if it touches the auxiliary protrusions and the interior surface of the rim, in which case there are three retaining points for the bottle. The positions of the stop faces placed on the rim of the frame may vary in the framework of the invention. The essential point is that a bottle placed in the frame is retained by the auxiliary protrusions and at least one stop face placed on the opposite side of the bottle. Supposing the auxiliary protrusions of adjacent partitions are connected with a straight line and a bottle diameter parallel to this line is drawn, the stop face must be placed on the opposite side of this diameter with respect to the auxiliary protrusions.

Between the rings 3 and 13 forming the rim of the frame 2 there is a gap 26, allowing a bar code 28 glued to the side of the vessel 4 or bottle 8 to be read. The bar code holds data related to the nature and quantity of reagent contained in the vessel or bottle.

The vessel and bottle have orifices 22 and 23 provided with threaded caps (not shown). The orifices lie at essentially equal distances from the center of the frame when the vessel and bottle are in place in the frame. The vessel 4 has a handle 20 on its top, permitting easy removal of the vessel from the frame.

Figure 3:
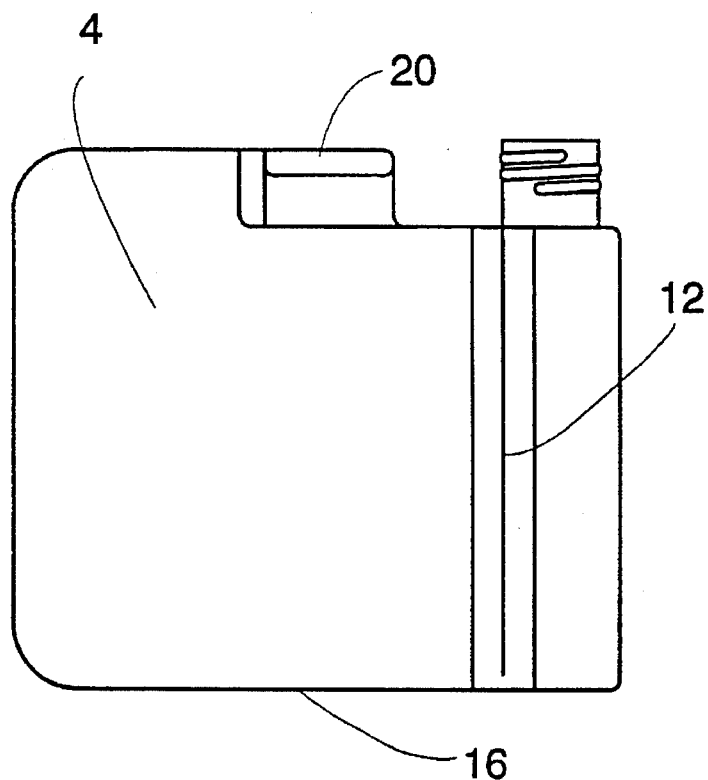
FIG. 3 presents a sectorial reagent vessel in side view.
Figure 5:
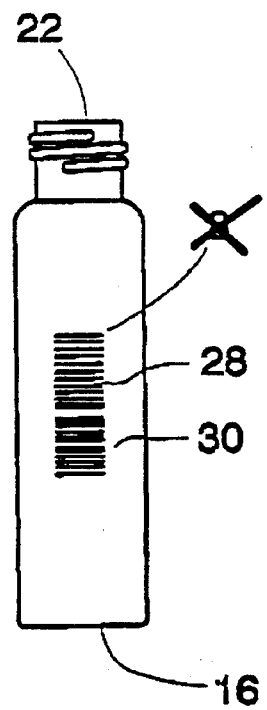
FIG. 5 presents a sectorial reagent vessel in front view.
Figure 4:
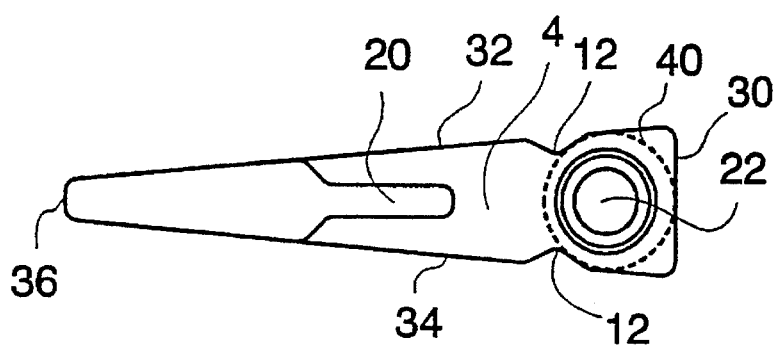
FIG. 4 presents a sectorial reagent vessel in top view.

FIGS. 3, 4 and 5 depict a reagent vessel 4 in side view, in top view and in front view. The vessel has a front wall 30 and side walls 32 and 34 forming an acute angle with the front wall. The side walls are joined with the narrow back wall 36 of the vessel. The tops of the walls are joined with a cover, on which the handle 20 of the vessel is formed. In a certain position in each side wall of the vessel 4 there is a recess 12 extending across the entire height of the vessel. The groove 12 is so placed in the side wall that an imaginary circle 40 corresponding to the basal area of the vessel is tangent with the sides of the groove and the front wall. Glued to the front wall 30 of the vessel 4 is a bar code 28.

The storing places 14 delimited by the partitions 6 are so designed that the circular frame 2 will accommodate as many vessels 4 or bottles 8 as possible. The auxiliary protrusions 10 in the partitions 6 are so placed that they form a seat for a round bottle 8 of a diameter as large as possible that fits into the storing place 14, such that the bottoms of the vessels 4 and bottles 8 will be at the same height and their orifices at the same distance from the center of the frame, obviating the need for separate guides. Since no separate guides are needed for round bottles, the reagent store is considerably easier to handle than in generally known solutions.

Although the invention has been described above by the aid of one of its embodiments, the presentation is not to be regarded as constituting a limitation of the scope of patent protection, but the embodiments of the invention may vary within the limits defined by the following claims.

We claim:

1. Wedge-shaped reagent vessel comprising a front wall and two side walls joined with the front wall and forming an acute angle with the front wall, a bottom of the vessel extending between the two side walls, each side wall being provided with a vertical recess placed at a distance from the front wall such that a circle fitted inside the bottom of the vessel is tangent with the recesses and the front wall, an interior of the vessel being formed by the front wall, the two side walls and the bottom of the vessel.

2. The reagent vessel as defined in claim 1, wherein the front wall of the reagent vessel is provided with a code holding data identifying the reagent vessel.

3. The reagent vessel as defined in claim 1, further comprising a cover part joining the two side walls of the reagent vessel and a handle, the handle being provided on the cover part.

4. The reagent vessel as defined in claim 1, wherein the vertical recesses extend from a bottom to a top of the two side walls of the reagent vessel.

5. The reagent vessel as defined in claim 1, further comprising a cover part joining the two side walls of the reagent vessel, the cover part having only one opening therein.

6. The reagent vessel as defined in claim 5, wherein the opening in the cover part is the only opening to the interior of the vessel.

7. The reagent vessel as defined in claim 1, wherein the wedge-shaped reagent vessel has a triangular configuration, the two side walls tapering toward one another from the front wall and each side wall having a first end adjacent the front wall and a second end distal from the first end, a width of the vessel being a minimum at the second ends of the side walls.

8. The reagent vessel as defined in claim 1, wherein the two side walls of the reagent vessel are generally planar except for the vertical recesses in the two side walls, the two side walls extending between the bottom of the vessel to a top of the vessel.

9. Wedge-shaped reagent vessel comprising a front wall, two side walls, a back wall and a bottom, the two side walls being joined with the front wall and forming an acute angle with the front wall, the bottom of the vessel extending between the two side walls, each side wall being provided with a vertical recess placed at a distance from the front wall such that a circle fitted inside the bottom of the vessel is tangent with the recesses and the front wall, the two side walls engaging the front wall and the back wall and tapering from the front wall to the back wall, a distance between ends of the back wall adjacent the side walls being a maximum width of the back wall.

10. The reagent vessel as defined in claim 9, wherein the front wall of the reagent vessel is provided with a code holding data identifying the reagent vessel.

11. The reagent vessel as defined in claim 9, further comprising a cover part joining the two side walls of the reagent vessel and a handle, the handle being provided on the cover part.

12. The reagent vessel as defined in claim 9, wherein the vertical recesses extend from a bottom to a top of the reagent vessel.

13. The reagent vessel as defined in claim 9, further comprising a cover part joining the two side walls of the reagent vessel, the cover part having only one opening therein.

14. The reagent vessel as defined in claim 13, wherein the opening in the cover part is the only opening to an interior of the vessel.

15. The reagent vessel as defined in claim 9, wherein a distance between the side walls is smallest adjacent the back wall.

16. The reagent vessel as defined in claim 9, wherein the two side walls of the reagent vessel are generally planar except for the vertical recesses in the two side walls, the two side walls extending between the bottom of the vessel to a top of the vessel.

17. The reagent vessel as defined in claim 9, wherein the vertical recesses are closer to the front wall than the back wall.

* * * * *